United States Patent
Gerhardt et al.

(10) Patent No.: US 10,603,458 B2
(45) Date of Patent: Mar. 31, 2020

(54) WEAR-OUT INDICATOR FOR A PATIENT INTERFACE

(71) Applicant: KONINKLIJKE PHILIPS N.V., Eindhoven (NL)

(72) Inventors: Lutz Christian Gerhardt, Eindhoven (NL); Sima Asvadi, Eindhoven (NL); Joyce Van Zanten, Waalre (NL); Mareike Klee, Straelen (DE); Robert William Baiko, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 693 days.

(21) Appl. No.: 15/324,919

(22) PCT Filed: Jul. 8, 2015

(86) PCT No.: PCT/EP2015/065642
§ 371 (c)(1),
(2) Date: Jan. 9, 2017

(87) PCT Pub. No.: WO2016/005473
PCT Pub. Date: Jan. 14, 2016

(65) Prior Publication Data
US 2017/0216548 A1 Aug. 3, 2017

Related U.S. Application Data

(60) Provisional application No. 62/079,034, filed on Nov. 13, 2014.

(30) Foreign Application Priority Data

Jul. 10, 2014 (EP) .................................... 14176465
Jan. 14, 2015 (EP) .................................... 15151168

(51) Int. Cl.
*A61M 16/06* (2006.01)
*A61M 16/00* (2006.01)

(52) U.S. Cl.
CPC .... *A61M 16/0683* (2013.01); *A61M 16/0057* (2013.01); *A61M 16/0605* (2014.02);
(Continued)

(58) Field of Classification Search
CPC .............. A61M 16/06; A61M 16/0605; A61M 16/0616; A61M 16/0633; A61M 16/0683;
(Continued)

(56) References Cited

U.S. PATENT DOCUMENTS

| 7,422,256 B2 * | 9/2008 | Mueller | .................... B66C 1/18 294/74 |
| 7,938,468 B2 * | 5/2011 | Mueller | .................... B66C 1/18 294/74 |

(Continued)

FOREIGN PATENT DOCUMENTS

| CA | 2835491 A1 | 11/2012 |
| EP | 1902743 A1 | 3/2008 |

(Continued)

OTHER PUBLICATIONS

Cambridge University: "Polymer Opals", pp. 1-8, May 28, 2013 (May 28, 2013), XP054975867, URL:https://youtu.be/UgGQjWRKRz8, retrieved on Apr. 29, 2015].

(Continued)

*Primary Examiner* — Tu A Vo
(74) *Attorney, Agent, or Firm* — Michael W. Haas

(57) ABSTRACT

The present invention relates to a member (14, 24, 26) of a patient interface (10) for providing a flow of breath-able gas to a self-ventilating patient (12). The member (14, 24, 26) includes a wear-out indicator (32) for indicating a wear-out of the member (14, 24, 26) to the patient (12). The wear-out
(Continued)

indicator (32) includes an elastic structure (34) that appears in a first colour in an unstressed condition and is configured to re-versibly change its apparent colour when being stretched and re-turned to its unstressed condition again. The elastic structure (34) is configured to indicate a wear-out of the member (14, 24, 26) by appearing in a second colour in its unstressed condition when the structure (34) has lost at least a part of its elasticity, wherein the second colour is different from the first colour.

14 Claims, 5 Drawing Sheets

(52) U.S. Cl.
CPC .... *A61M 16/0616* (2014.02); *A61M 16/0633* (2014.02); *A61M 2205/0227* (2013.01); *A61M 2205/584* (2013.01); *A61M 2210/04* (2013.01)
(58) Field of Classification Search
CPC ........ A61M 16/0688; A61M 2205/584; A61M 2205/0227; A42B 1/00; A62B 18/00; A62B 18/02; A62B 18/04; A62B 18/08; A62B 18/084; A62B 18/088; A62B 9/006; A61F 9/02
See application file for complete search history.

(56) References Cited

U.S. PATENT DOCUMENTS

| | | | |
|---|---|---|---|
| 8,695,602 B2 | 4/2014 | Pierro | |
| 2006/0246802 A1 | 11/2006 | Hughes | |
| 2008/0060649 A1* | 3/2008 | Veliss | A61M 16/0825 |
| | | | 128/205.25 |
| 2008/0149099 A1 | 6/2008 | Doyle | |
| 2009/0012207 A1 | 1/2009 | Leyrer | |
| 2009/0199857 A1 | 8/2009 | Peake | |
| 2010/0000534 A1* | 1/2010 | Kooij | A61M 16/0666 |
| | | | 128/204.18 |
| 2010/0018534 A1* | 1/2010 | Veliss | A61M 16/06 |
| | | | 128/206.24 |
| 2010/0024098 A1 | 2/2010 | Chiang | |
| 2011/0197341 A1 | 8/2011 | Formica | |
| 2012/0067349 A1* | 3/2012 | Barlow | A61M 16/06 |
| | | | 128/205.25 |
| 2012/0150511 A1 | 6/2012 | Frantti et al. | |
| 2012/0199131 A1 | 8/2012 | Sofranko | |
| 2012/0285448 A1* | 11/2012 | Dugan | A61M 16/06 |
| | | | 128/202.16 |
| 2012/0285455 A1* | 11/2012 | Varga | A61B 5/0836 |
| | | | 128/204.21 |
| 2012/0285457 A1* | 11/2012 | Mansour | A61M 16/06 |
| | | | 128/205.12 |
| 2012/0285461 A1 | 11/2012 | Pierro | |
| 2012/0285464 A1 | 11/2012 | Birch | |
| 2012/0289838 A1* | 11/2012 | Varga | A61B 5/0836 |
| | | | 600/473 |
| 2012/0289851 A1* | 11/2012 | Varga | A61M 16/0605 |
| | | | 600/532 |

FOREIGN PATENT DOCUMENTS

| | | |
|---|---|---|
| JP | 2006028202 A | 2/2006 |
| JP | 2007516749 A | 6/2007 |
| JP | 2014079383 A | 5/2014 |
| RU | 2009104951 A | 8/2010 |
| WO | WO2005063327 A1 | 7/2005 |
| WO | WO2009109005 A1 | 9/2009 |
| WO | WO2011077254 A2 | 6/2011 |
| WO | WO2013079955 A1 | 6/2013 |
| WO | WO2014142681 A1 | 9/2014 |

OTHER PUBLICATIONS

Ito T. et al., "Strain-Responsive Structural Colored Elastomers by Fixing Colloidal Crystal Assembly", Department of Materials Science and Engineering, Nagoya Institute of Technology, Gokiso-cho, Showa-ku, Nagoya 466-8555, Japan, Langmuir, 2013, 29 (45), pp. 13951-13957, DOI: 10.1021/la4030266, Publication Date (Web): Oct. 7, 2013 Copyright © 2013 American Chemical Society.

* cited by examiner

WEAR-OUT INDICATOR FOR A PATIENT INTERFACE

CROSS-REFERENCE TO RELATED APPLICATIONS

This patent application claims the priority benefit under 35 U.S.C. § 371 of international patent application no. PCT/EP2015/065642, filed Jul. 8, 2015, which claims the priority benefit under 35 U.S.C. § 119(e) of U.S. Provisional Application No. 62/079,034 filed on Nov. 13, 2014, and which claims the benefit of European Application No. EP15151168.0 filed Jan. 14, 2015 and European Application No. EP14176465.4 filed Jul. 10, 2014. These applications are hereby incorporated by reference herein.

FIELD OF THE INVENTION

The present invention relates to a member of a patient interface which visually indicates a user that the member and/or the patient interface needs to be replaced due to long-term usage and related functionality changes of materials. Further, the present invention relates to a patient interface and to a pressure support system including such a member.

BACKGROUND OF THE INVENTION

Patient interfaces, such as masks in pressure support systems, are used for delivering gas to a user. Such gases like air, cleaned air, oxygen, or any modification thereof are submitted to the user (also referred to as patient) via the patient interface in a pressurized or unpressurized way.

For several chronic disorders and diseases the usage of such a patient interface is necessary or at least advisable.

One example of such a disease is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a tube and a machine that blows pressurized gas, preferably air, into the patient interface and through the airway of the patient in order to keep it open. Positive air pressure is thus provided to a patient through a hose connected to a patient interface or respiratory interface, such as a face mask, that is worn by the patient regularly at night. The afore-mentioned long-term use of the patient interface is the result, since the wearing of the patient interface usually takes place during the sleeping time of the patient.

Examples for patient interfaces are:
nasal masks, which fit over the nose and deliver gas through the nasal passages,
oral masks, which fit over the mouth and deliver gas through the mouth,
full face masks, which fit over both, the nose and the mouth, and deliver gas to both, and
nasal pillows, which are regarded as masks as well within the scope of the present invention and which consist of small nasal inserts that deliver the gas directly to the nasal passages.

In order to guarantee a reliable operation of the device, the patient interface needs to closely fit on the patient's face to provide an air-tight seal at the mask-to-face interface. The patient interface is worn using a headgear with straps that go around the back of the patient's head. These straps are often made of an elastic textile material. The patient interface or mask in practice usually comprises a soft cushion that is used as mask-to-patient interface, i.e. that contacts the face of the patient when the mask is worn, as well as it usually comprises a so-called mask shell building a rigid or semi-rigid holding structure for holding the cushion in place and for supplying mechanical stability to the patient interface.

The cushion usually comprises one or more pads made of gel or silicone or any other soft material in order to increase the patient comfort and guarantee a soft feeling on the patient's face. The latter-mentioned mask shell is usually made of polycarbonate and normally further comprises a hose interface that is adapted for connecting the air supplying hose to the mask. Depending on the type of the mask, it may also comprise a mechanism with an additional cushion support on the forehead (also denoted as forehead support) to balance the forces put by the mask around the airway entry features of the human face.

During use, mask materials can degrade and finally wear out. Such a degradation or wear-out may decrease the overall mask performance. During use, the headgear can lose at least a part of its elasticity and can change its mechanical properties, such as tensile strength and/or level of elongation under stress, all of which can result in reduced therapy compliance and patient comfort. There is especially a risk for higher leakage and skin damage or red marks, since higher strapping forces are needed to make a mask leak-tight on the face with a worn-out headgear. Although there is a possibility for OSA patients to regularly replace their mask or components thereof through new products, many patients do not make use of this option.

U.S. 2012/0285464 A1 discloses a headgear with straps that are configured to change colour in response to a level of force induced stress on the straps. This shall help to visually indicate the patient an over tightening of straps which could otherwise cause necrosis if not loosened. However, a tension indicator as disclosed in U.S. 2012/0285464 A1 is not essential for the patient, since the patients directly feel the tension and therefore usually recognize themselves when the headgear straps are over tightened. Visual inspection of the tension indicator may also be difficult while the headgear is being worn. On the other hand, a wear-out of parts of the patient interface is much more difficult to detect for a patient. Usually this may not be recognized in an intuitive way.

U.S. 2012/0285461 A1 discloses a mask for patient ventilation, wherein the mask includes a headgear with a side strap that may change colors or change from opaque to somewhat translucent in response to a level of force induced stress on the strap which is indicative of a level of force or strap tightening that is considered to be so tight as to cause necrosis if not loosened.

WO 2014/142681 A1 discloses a nasal cannula assembly with a headgear strap that includes a tightness indicator which provides the user with feedback regarding whether the tightness of the headgear strap is inside or outside a desired tightness range (too tight or too loose).

To overcome these problems, objective replacement indicators are required that are directly coupled to the level of wear-out. There is thus a need for objective and reliable wear-out indicators that may be easily applied in a patient interface and that give the patient a clear and easily comprehensible feedback when he/she should replace parts of the patient interface.

SUMMARY OF THE INVENTION

It is an object of the present invention to provide a member of a patient interface that includes an objective wear-out/replacement indicator that is directly coupled to the level of wear-out, inexpensive and obvious to the patient.

In a first aspect of the present invention, a member of a patient interface for providing a flow of breathable gas to a self-ventilating patient is presented, wherein said member comprises a wear-out indicator for indicating a wear-out of the member to the patient. The wear-out indicator comprises an elastic structure that appears in a first colour in an unstressed condition and is configured to reversibly change its apparent colour when being stretched and returned to its unstressed condition again. The elastic structure is configured to indicate a wear-out of the member by appearing in a second colour in its unstressed condition (i.e., when the headgear or mask is not used/worn) when the structure has lost at least a part of its elasticity, wherein the second colour is different from the first colour. The (reversible) colour change of the elastic structure may be either gradual or abrupt. Preferably, it is a gradual colour change. When the member of the patient interface is worn out (e.g. shows typically higher residual strain), there is a permanent colour change (associated with an irreversible backshift in colour).

In a further aspect of the present invention, a patient interface for providing a flow of breathable gas to a self-ventilating patient is presented, wherein the patient interface comprises a member of the above-mentioned type.

In a still further aspect of the present invention, a pressure support system is presented that comprises a pressure generator for generating a flow of breathable gas and a patient interface for providing the flow of breathable gas to a self-ventilating patient, wherein the patient interface comprises a member of the above-mentioned type.

Preferred embodiments of the invention are defined in the dependent claims. It shall be understood that the claimed patient interface and the claimed pressure support system have similar and/or identical preferred embodiments as the claimed member of the patient interface and as defined in the dependent claims.

The present invention provides a member of a patient interface that includes a user-friendly wear-out indicator that visibly indicates the patient that the member is worn out. The patient thus receives a visual feedback that helps him/her recognizing that the member of the patient interface has lost its functionality and has to be replaced by a new one. The color change may be either recognized by the human eye without any further required auxiliary means or e.g. by making a photo with a camera that is connected to any type of computing device which analyzes the colour change and gives the user an automatic feedback. Various other feedback methods are possible.

The member itself may be any part or element of a patient interface. The member may, for example, be a headgear strap of a patient interface or a cushion element of a patient interface. However, the member could also be realized as another part of a patient interface that is exposed to forces during usage and may therefore get worn out after a long-term usage (fatigue, plastic deformation, shape change).

The wear-out indicator included in the member of the patient interface comprises an elastic structure which appears in a first colour in an unstressed condition, i.e. as long as it is not used and no forces are applied to it. "Elastic" shall herein mean that said structure of the wear-out indicator is elastically deformable in a reversible manner. As soon as an external force is applied to the elastic structure, it will deform. Once the force is no longer applied, the object returns to its original colour and shape (as long as the elastic behaviour of the structure is present).

As long as the elasticity of the elastic structure is preserved, the elastic structure appears in a first colour when being in its unstressed condition. If the elastic structure is then stretched and purely elastically deformed/expanded, the elastic structure will change its apparent colour. This colour change is a reversible colour change after strain release. This means that the elastic structure will appear in its original first colour when being returned to its unstressed condition again.

It shall be furthermore noted that the term "apparent colour" shall mean the colour of the elastic structure that is visible to the patient from outside. The reversible colour change may thus either be caused by a change of the colour of the material of the elastic structure or by an overall colour variation of the member that is caused by a part of the elastic structure that only becomes apparent when the elastic structure is being stretched. The colour change is thus not necessarily a change of the colour of the material of the elastic structure. However, it is important that the colour change is reversible as long as the elasticity of the elastic structure is preserved.

As soon as the elastic structure loses a part of its elasticity, e.g. due to a long-term usage and an accompanying wear-out of the material, the elastic structure will not return any longer to its original colour and/or shape when being in its unstressed condition. If this is the case, the elastic structure will not return to the first colour anymore when being unstressed, but will appear in its unstressed condition in a second colour that is different from the first colour. In other words, as soon as the elastic structure becomes worn out and loses a part of its elasticity, the colour in which it appears when being unstressed (when not being used) has irreversibly changed to a second colour that is different from the first colour in which it appears in its unstressed condition as long as the full elasticity of the elastic structure is preserved. Whereas the colour change of the elastic structure is preferably gradual (over rainbow spectrum), the colour change caused by appearance of a second colour can also be abrupt (switching between two colours, e.g. green to blue). Users may thus perform regular checks by observing the apparent colour of the member when the member is not in use. The user may, for example, take off the patient interface and then observe the colour in which the elastic structure appears. If this colour in the unstressed condition of the member has changed and does not appear anymore in its original colour, the user gets the feedback that he/she should replace the member. The patient thus receives an easy visible feedback by a colour change, wherein the colour change is directly coupled to the level of wear-out of the member.

As long as the elasticity of the member is preserved, the elastic structure may e.g. appear in yellow (orange/red) when it is not used (unstressed). As soon as the elastic structure is then stretched/expanded, the colour may e.g. change to green. If the member is then stretched/expanded even more, the colour of the elastic structure may change e.g. to blue. As long as the elasticity of the elastic structure is preserved, the colour will return in this example to yellow (orange/red) again as soon as the member is not stretched anymore. If the member gets worn out after a certain time or quantity of usages of the patient interface, it will not anymore return to its original shape, since it has lost a part of its elasticity. In the above-mentioned example it would then e.g. appear in green in its unstressed condition, and not anymore in yellow. The colour change is thus directly related to the residual strain level, indicating functionality change and wear out of the member.

According to an embodiment of the present invention, the first and the second colour are primary or secondary colours. "Primary colours" are sets of colours that can be combined to make a useful range of colours. "Secondary colours" are mixed colours of primary colours either by additive or subtractive colour mixing. It is especially preferred that the second colour is not a secondary colour of the first colour mixed with white. In other words, it is especially preferred that the colour change indicated by the wear-out indicator is not simply a change of the first colour becoming brighter or darker. It is especially preferred that the wear-out is indicated by an easy recognisable change of the colour, e.g. from yellow to green, from yellow to blue, from yellow to red, from red to green, etc. This helps to give the patient a clear and definite feedback if, or if not, the member has to be replaced.

According to a further embodiment of the present invention, the member comprises multiple wear-out indicators that are arranged in segments which are distributed over the member and spaced apart from each other. In case of a headgear strap, the headgear strap may e.g. comprise several spaced apart segments in each of which a wear-out indicator of the above-mentioned type is arranged. In this case the user may receive the feedback which part of the headgear strap is worn out. This might also help the user to understand where in the headgear the most internal stresses occur during usage and which parts of the headgear are more sensitive to get worn out compared to others.

According to a further embodiment, the elastic structure comprises a photonic crystal material. Such photonic crystal materials are materials that change colour when being stretched. This colour change is a reversible colour change of the above-mentioned type. Photonic crystal materials are also denoted as colloidal photonic crystals, polymer opals and strain-responsive structural coloured elastomers. Other possible material candidates could be liquid crystal polymers or any other smart, strain-responsive material responding to mechanical trigger with a colour change.

Materials of this type are known from Cambridge Enterprises, Polymer Opals stretch-to-change colour, retrieved from the internet on September 29 [http://www.enterprise.cam.ac.uk/industry/licensing-opportunities/polymer-opals-elastic-colour/], or from Ito et al.: "Strain-Responsive Structural Colored Elastomers by Fixing Colloidal Crystal Assembly" Langmuir, 2013. Further examples of these materials are known from U.S. 2009/012207 A1 and from WO 2013/079955 A1.

Colloidal photonic crystals are embedded in an elastic matrix and change colour due to changes in lattice spacing when stretched. Polymer opals are new materials that produce a range of pure, vibrant colours solely through their structure. Polymer opals use hard polymeric spheres bonded to a rubber-like outer shell. When processed correctly, the shell material forms an elastic matrix and the hard spheres become ordered into durable, impact-resistant photonic crystals. The colour is produced by selective reflection of illuminating light. Polymer opals can be made to produce any colour on the visible spectrum, and even beyond. Stretching shifts the colour e.g. from yellow towards green and finally towards blue. The material itself is elastic and will completely return to its original colour on release as long as it is not worn out, i.e. as long as the material has not lost its elasticity.

According to an embodiment, the elastic structure may comprise an elastic base layer which is coated by the photonic crystal material, or a matrix in which the photonic crystal technology (or any other mentioned above) are embedded. The elastic base layer may e.g. comprise silicon, a silicon gel or any other soft material. The photonic crystal material may e.g. be heat-laminated onto this elastic base layer. In this case, the photonic crystal material "only" builds the visible top surface of the member. The elastic base layers may also comprise an elastic yarn or elastic fibres which are coated with the photonic crystal material.

According to a further embodiment, the photonic crystal material is arranged within the elastic structure in a corrugated pattern or in a zigzag pattern. An arrangement in such a pattern provides the further advantage that the wear-out of the member may not only be indicated by means of a colour change, but also by means of a shape change of the pattern. If the presented member gets worn out/stretched out, the pattern of the photonic crystal material within the elastic structure will not appear as a corrugated pattern or zigzag pattern anymore, but rather become a flat pattern that gives a clear indication to the patient to replace the headgear or any other member of the patient interface. It is clear that patterns other than a corrugated pattern or a zigzag pattern are possible as well.

According to a further embodiment, the elastic structure comprises a knitted fabric, wherein neighbouring wales or courses have a visually distinct coloration, and wherein neighbouring wales or courses are arranged in different layers and have different colours. Such a two-coloured wale knit structure (made of coloured fibres) may be used as an alternative to the above-mentioned photonic crystal material. The principle of the wear-out indicator, however, remains the same. The knitted fabric also undergoes a loss of elasticity and performs a reversible colour "switch" (appearance of two colours in stretched state, appearance of one colour in un-stretched state) when being stretched and returned to its unstressed condition again, as long as the elasticity of the structure is preserved. As soon as the structure loses a part of its elasticity, the colour change will be irreversible in the unstressed condition. As long as neighbouring wales or courses have different colours and are arranged in different layers, the colour of the underlying, hidden web structure may only become visible and is revealed when the elastic structure is expanded. If the elastic structure is worn out, the underlying hidden rib structure having the second colour is even visible in the unstressed condition, such that the patient receives the feedback to replace the member by a new one.

BRIEF DESCRIPTION OF THE DRAWINGS

These and other aspects of the invention will be apparent from and elucidated with reference to the embodiments described hereinafter. In the following drawings

FIG. 2 schematically shows the member according to the present invention including a wear-out indicator according to a first embodiment, wherein

FIG. 3 schematically shows the member according to the present invention including a wear-out indicator according to a second embodiment, wherein

FIG. 4 schematically shows the member according to the present invention including a wear-out indicator according to a third embodiment, wherein FIG. 5 schematically shows the member according to the present invention including a wear-out indicator according to a fourth embodiment, wherein

DETAILED DESCRIPTION OF THE INVENTION

Figure 1:
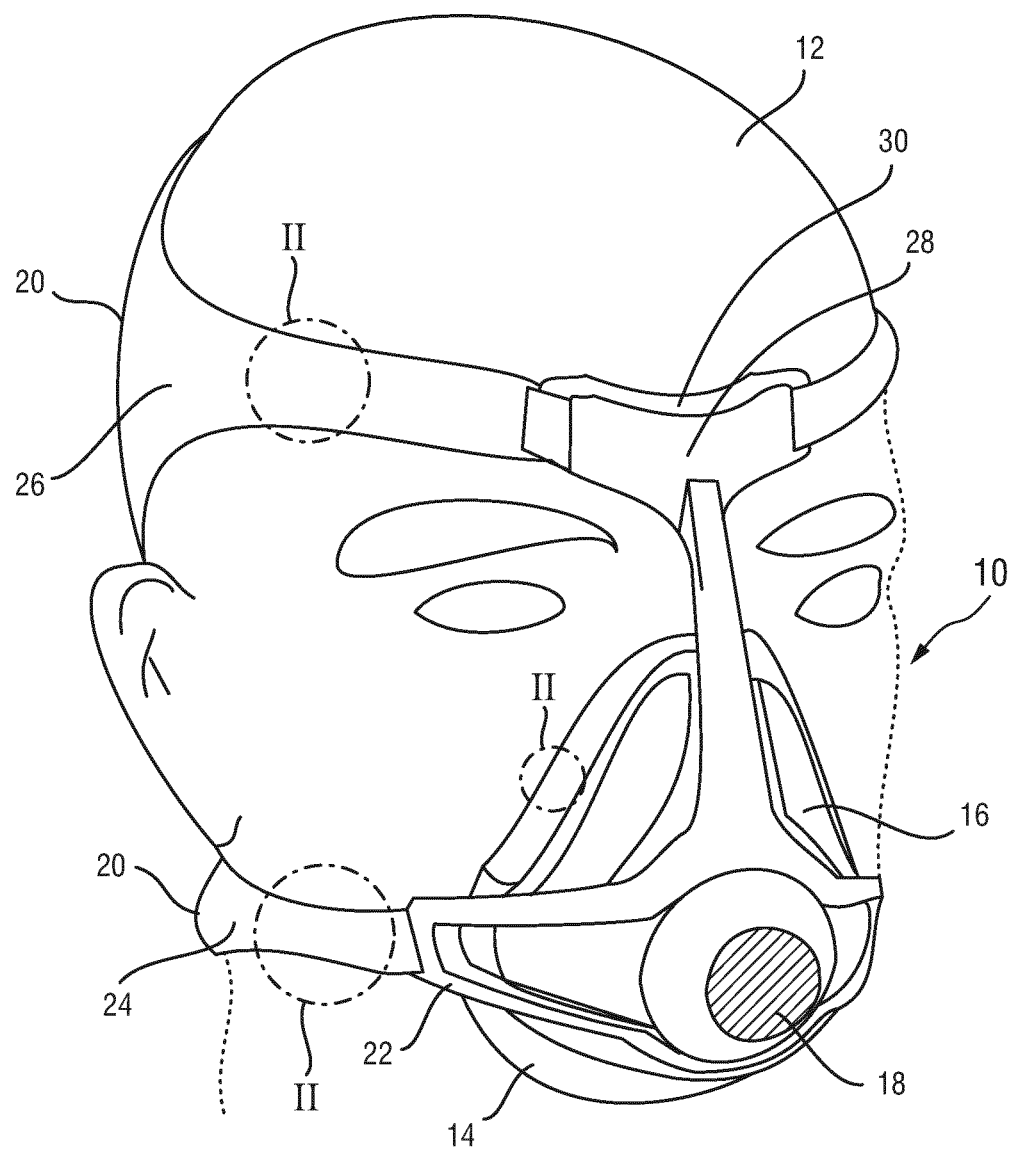
FIG. 1 shows an exemplary embodiment of a patient interface in which a member according to the present invention may be applied.

FIG. 1 shows an exemplary embodiment of a patient interface for delivering a flow of breathable gas to a patient. The patient interface is therein in its entirety denoted by reference numeral 10.

In this embodiment the patient interface 10 is designed as a full-face mask covering the mouth and the nose of a patient 12. It shall be noted that the patient interface 10 may alternatively be designed as a nose mask, a mouth mask or as a total face mask without leaving the scope of the present invention.

The patient interface 10 comprises a cushion element 14 and a mask shell 16. The cushion element 14 is designed to contact the face of the patient 12 and to provide an air-tight seal at the interface between the patient's face and the patient interface 10. The cushion element 14 usually comprises a soft material, like silicone or any other rubber or suitable elastic material. The mask shell 16 provides a flexible, semi-rigid or rigid support structure for holding the cushion element 14. The mask shell 16 is usually connected to the backside of the cushion element 14, wherein the backside is meant to denote the side of the cushion element 14 opposite the side of the cushion element 14 contacting the patient's face during use. The mask shell 16 may either be releasably or fixedly connected to the cushion element 14. The cushion element 14 and the mask shell 16 thus together form a cavity which is in this case designed to receive the mouth and the nose of the patient 12. It shall be noted that the cushion element 14 and the mask shell 16 may alternatively be formed as one integral piece.

On the opposite side directing away from the patient's face, the mask shell 16 preferably comprises a connector 18. Via this connector 18, the patient interface 10 may be connected to a hose (not shown) via which a pressurized flow of breathable gas can be submitted to the patient interface 10. The mask shell 16 comprises a rigid frame 22 and is further connected to a headgear 20. This headgear 20 is used for attaching the patient interface 10 to the patient's head. According to the exemplary embodiment shown in FIG. 1, the headgear 20 is made of a two lower and upper elastic headgear straps 24, 26. These lower and upper headgear straps 24, 26 may be connected to the frame 22 of the headgear 20 and used for donning the mask shell 16 and the cushion element 14 to the patient's face.

In the illustrated example the headgear 20 furthermore comprises a forehead support 28. This forehead support 28 allows stabilizing the patient interface 10 while being donned to the patient's face. The forehead support 28 reduces the pressure that is exerted onto the patient's nose during use. In order to make the forehead support 28 as comfortable as possible, the forehead support 28 furthermore comprises a forehead cushion 30 which is attached thereto.

One of the central features of the present invention is a wear-out indicator that indicates a wear-out of a part/member of the patient interface 10. Said wear-out indicator may be comprised in one of the headgear straps 24, 26 or in the cushion element 14, as this is indicated in FIG. 1 by detail II.

Figure 2A:
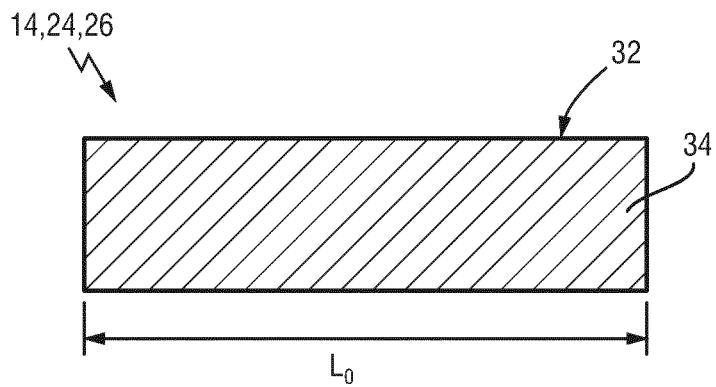
FIG. 2A shows the member in an unstressed condition and FIGS. 2B and 2C show the member when being expanded.
Figure 2B:
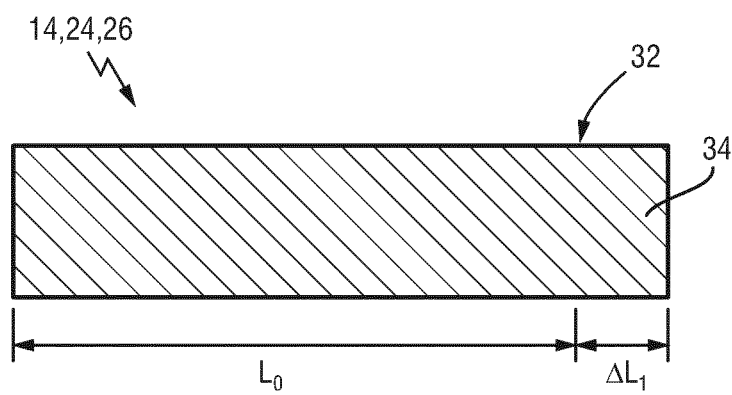
Figure 2C:
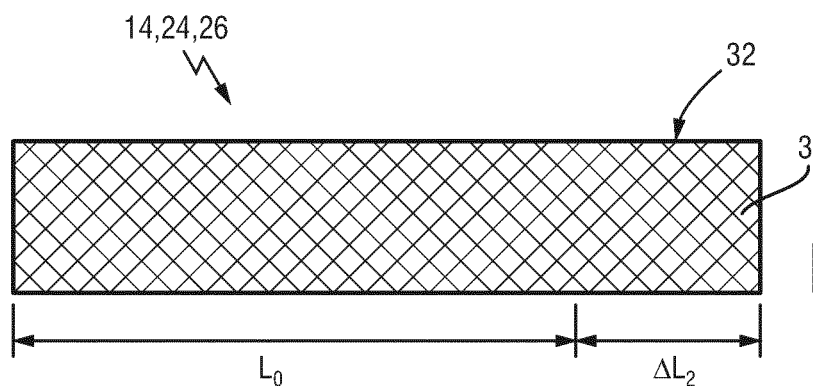

A first embodiment of such a wear-out indicator is shown in FIGS. 2A-2C. The wear-out indicator 32 comprises an elastic structure 34. FIG. 2A shows an unstressed condition of the elastic structure 34, i.e. a condition in which no load is applied to the elastic structure 34. In this condition the elastic structure 34 has a length $L_0$ which is also denoted as reference length. The wear-out indicator according to the first embodiment further comprises a photonic crystal based polymer material (or any other colour changing strain responsive material mentioned before) that is either integrated into the elastic structure 34 or heat-laminated onto the elastic structure 34. Such a photonic crystal-based polymer material has the characteristic that it changes its apparent colour (in a colour range visible by naked eye) when being extended/stretched. The colour change is thus directly coupled to the level of extension of the material. Colloidal photonic crystals are embedded in an elastic matrix and change colour due to changes in lattice spacing when stretched. They can be made to produce any colour on the visible spectrum. The colour change is a reversible colour change, meaning that the photonic crystal-based polymer material itself is elastic and will completely return to its original colour after strain release when it returns back into its unstressed condition.

In the unstressed condition shown in FIG. 2A the elastic structure 34 appears in a first colour, e.g. in yellow. As soon as the elastic structure is stretched, e.g. by $\Delta L_1$ as shown in FIG. 2B, it will change its apparent colour to another colour that is different from the first colour. In this situation it could e.g. appear in green. If the elastic structure 34 is stretched/extended even more, e.g. by $\Delta L_2$ as shown in FIG. 2C, it will further change its colour. In this situation it could e.g. appear in blue. In FIG. 2A-C, the different patterns denote different colours rather than real mechanical strain fields.

As long as the elastic structure 34 obtains its full elasticity, the elastic structure 34 will always return back into its reference length $L_0$ upon release. This also means that it will always return back to its first colour (in the above-mentioned example to yellow) upon release. However, as soon as the elastic structure 34 loses at least a part of its elasticity, i.e. as soon as the elastic structure 34 becomes less elastic, it will not anymore return back to its reference length $L_0$ upon release, but will have a longer length even when no external forces are applied to it. This is a clear indication that the elastic structure 34 loses its functionality and gets worn out. The wear-out indicator 32 will indicate this wear-out of the elastic structure 34 by then appearing in a second colour in its unstressed condition, wherein the second colour is different from the first colour.

The patient 12 may thus perform regular wear-out and replacement need checks by observing the colour of the wear-out indicator 32 when the headgear straps 24, 26 or the cushion element 14 are not in use. If the headgear straps 24, 26 or the cushion element 14 are worn out/stretched out, there will be an irreversible colour change, meaning that the colour of the wear-out indicator 32 does not return back to its original first colour when being released. The range of the colour change may even indicate the degree and severity of the wear-out state. In the above-mentioned example, a green colour in the unstressed condition (of a used/degraded headgear) of the elastic structure 34 could indicate a moderate wear-out and a blue colour in the unstressed condition of the elastic structure 34 could indicate a severe wear-out. However, it is clear that, depending on the characteristics of the photonic crystal-based polymer material, other colours could be realized as well. Nevertheless, it shall be noted that such a photonic crystal-based polymer material is able to achieve an easy recognisable colour changes from one colour to a totally different one and not only changing the brightness of a single colour, or vice versa.

Figure 3A:
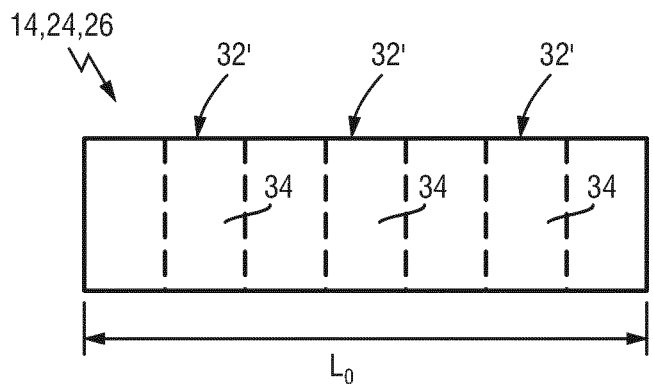
FIG. 3A shows the member in an unstressed condition and FIGS. 3B and 3C show the member when being expanded.
Figure 3B:
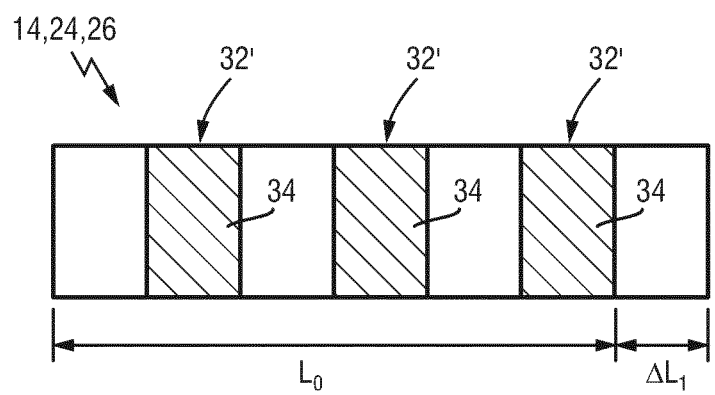
Figure 3C:
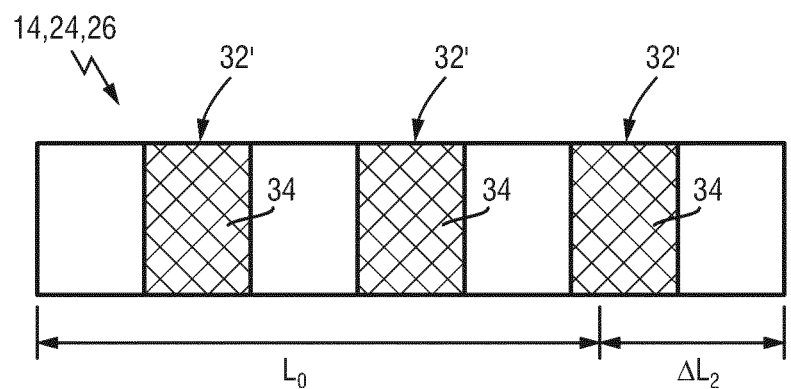

FIGS. 3A-3C show a second embodiment of a wear-out indicator according to the present invention. In this embodiment, the member 14, 24 and/or 26 of the patient interface 10 comprises multiple wear-out indicators 32' that are arranged in segments which are distributed over the member 14, 24, 26 and spaced apart from each other. In FIGS. 3A-3C these segments are shown as small rectangles. However, it is to be noted that the segment (patterns) may have any arbitrary shape and could also be round, quadratic, elliptical, linear etc. In this embodiment, wide polymer opal bands embedded in the substrate are revealed as a colour contrast on stretching. To obtain the strongest colour contrast, the colour of the polymer opal (32') in its unstressed state (shown in FIG. 3A) preferably has the same or similar colour as its underlying substrate (i.e., headgear fabric, 34). Each segment again comprises an elastic structure 34 which includes a photonic crystal-based polymer material that is either integrated into the elastic structure 34 or coated on top of it. FIGS. 3B and 3C show the member when be extended/stretched (by $\Delta L_1$ or $\Delta L_2$, respectively). The principle of the wear-out indication by means of a colour change in the unstressed condition of the elastic structure 34 remains the same as explained before. However, this embodiment provides the advantage that the patient 12 may receive an amplified/enhanced visual feedback by appearance of the segment (when worn out), and which segment of the member 14, 24, 26 gets worn out faster than another. This could help the patient to understand which parts of the headgear straps 24, 26 or the cushion element 14 are loaded most during use. On the other hand, this embodiment may also help the patient to simply replace parts of the member 14, 24, 26 that are worn out, whereas other parts of the member 14, 24, 26, which still provide their functionality, do not have to be replaced.

Figure 4A:
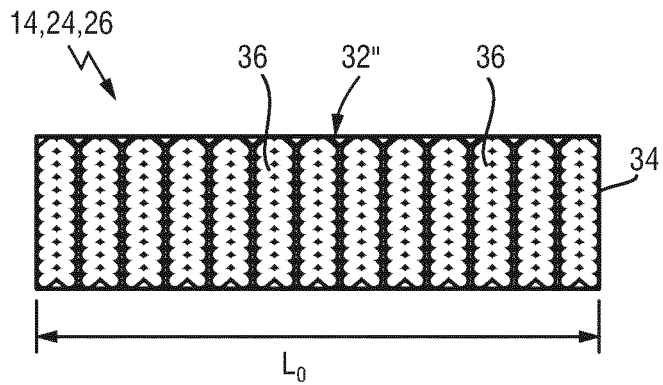
FIG. 4A shows the member in an unstressed condition and FIGS. 4B and 4C show the member when being expanded.
Figure 4B:
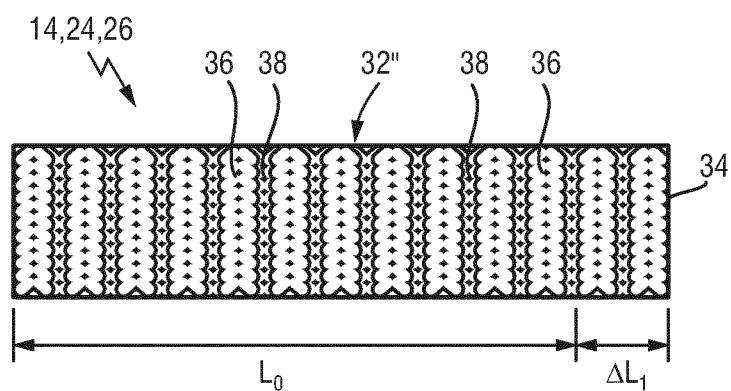
Figure 4C:
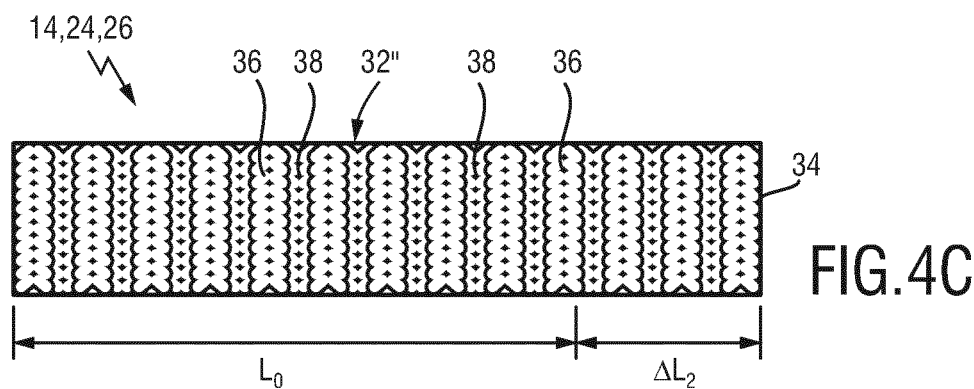

A third embodiment of a wear-out indicator 32" according to the present invention is shown in FIGS. 4A-4C. In this embodiment the elastic structure 34 comprises a knitted fabric. The knitted fabric is made of two differently coloured yarns. The fabric is knitted in such a way that neighbouring wales have a different colour, the knitwear consisting of alternating wales of, for example, red and white knit loops. A first type of wales 36 appears in a first colour and a second type of wales 38, which are arranged in-between the first type of wales 36, have a second colour. It is furthermore important that the first type of wales 36 are arranged in a different layer (depth) than the second type of wales 38. The second type of wales 38 are preferably arranged in an underlying layer that is arranged below the layer in which the first type of wales 36 are arranged. In the unstressed condition of the elastic structure 34 only the first type of wales 36 having the first colour are visible to the patient 12.

The second type of wales 38 having the second colour are in this situation hidden and therefore not visible to the patient 12. However, as soon as the elastic structure 34 gets stretched, the second type of wales 38 become more and more apparent such that the overall coloration of the member 14, 24, 26 changes. Similar as explained with respect to the first two embodiments, this coloration change (switch between one colour and two coloured knitwear) is a reversible change. The elastic structure 34 will thus appear in its first colour (the colour of the first wales 36) again as soon as it is released after usage. This will only be the case as long as the elastic structure 34 obtains its full elasticity. As soon as the elastic structure 34 becomes worn out, it will no longer return back into its original length $L_0$ upon release, but remain stretched out. The wear-out indicator 32" will indicate this stretch-out/wear-out by showing a second colour (the colour of the second type of wales 38). If both coloured yarns and wales have the same (mechanical) properties, the level of wear out can be directly linked to the width (length) of the coloured wale revealed from the initially invisible second colour. Again a direct coupling between wear out and functionality change of the member can be realised.

Figure 5A:
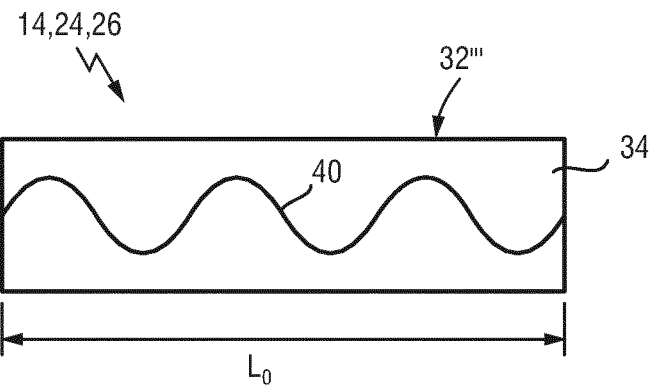
FIG. 5A shows the member in an unstressed condition and FIGS. 5B and 5C show the member when being expanded.
Figure 5B:
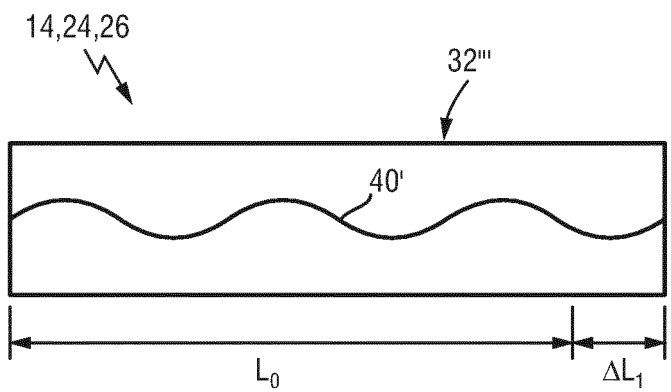
Figure 5C:
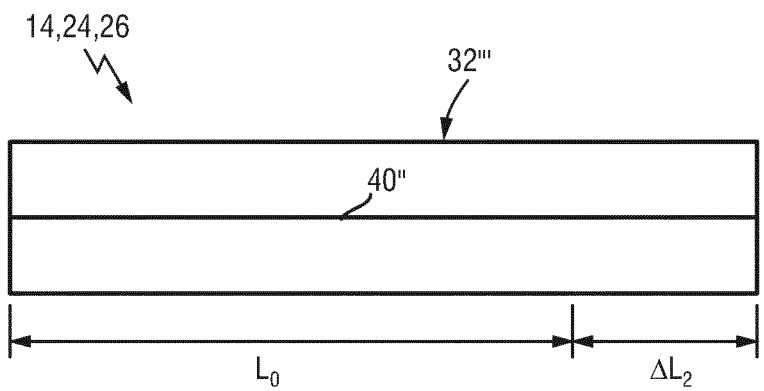

FIGS. 5A-5C show a fourth embodiment of a wear-out indicator 32''' according to the present invention. In this embodiment a wear-out indicator 32''' is used that does not only change its colour, but also its shape to indicate the wear-out of the member 14, 24, 26 to intensify the level of wear out and provide the user an enhanced visual feedback for wear out and replacement assessment. The elastic structure 34 in this embodiment comprises a photonic crystal-based polymer material that is arranged within the elastic structure 34 in a corrugated pattern 40 or in a zigzag pattern (FIGS. 5A-5C for simplicity reasons only show a corrugated pattern). Other patterns are of course possible as well. An elastic yarn comprising a polymer opal coating or colloidal photonic crystal coating may for example be stitched into the elastic structure 34 to form a corrugated or zigzag pattern. A deformation of the elastic structure 34 will in this case not only cause a colour change, as explained before with reference to FIGS. 2A-2C, but also a shaped change of the pattern 40 (see FIGS. 5B and 5C). The corrugated pattern 40 will more and more become a flat line upon expansion, as this is indicated by reference numerals 40' and 40". Similar as explained before, this colour and shaped change is only reversible as long as the elastic structure 34 obtains its full elasticity. A wear-out of the member 14, 24, 26 may thus be observed when the colour and the shape of the wear-out indicator 32''' in the unstressed condition of the member 14, 24, 26 has changed from its original colour/shape.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfil the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A member of a patient interface for providing a flow of breathable gas to a patient, said member comprising a wear-out indicator for indicating a wear-out of the member to the patient, wherein said wear-out indicator comprises an elastic structure that appears in a first colour in an unstressed condition and is configured to reversibly change the elastic structure's colour when being stretched and returned to the unstressed condition again, and wherein the elastic structure is configured to indicate a wear-out of the member by appearing in a second colour in the unstressed condition when the elastic structure has lost at least a part of the elastic structure's elasticity, wherein the second colour is different from the first colour.

2. The member according to claim 1, wherein the first and the second colour are primary or secondary colours in a visible colour spectrum.

3. The member according to claim 1, wherein the second colour is not a secondary colour of the first colour mixed with white.

4. The member according to claim 1, wherein the member comprises multiple wear-out indicators that are arranged in segments which are distributed over the member and spaced apart from each other.

5. The member according to claim 1, wherein the elastic structure comprises a photonic crystal material.

6. The member according to claim 5, wherein the elastic structure comprises an elastic base layer which is coated by the photonic crystal material.

7. The member according to claim 5, wherein the photonic crystal material is arranged within the elastic structure in a periodic or corrugated pattern.

8. The member according to claim 5, wherein the photonic crystal material is arranged within the elastic structure in a zigzag pattern.

9. The member according to claim 1, wherein the elastic structure comprises a knitted fabric, wherein neighbouring wales or courses of the knitted fabric have a different coloration.

10. The member according to claim 9, wherein the neighbouring wales or courses are arranged in different layers.

11. The member according to claim 1, wherein the member is a headgear strap of a patient interface.

12. The member according to claim 1, wherein the member is a cushion element of a patient interface.

13. A patient interface for providing a flow of breathable gas to a self-ventilating patient comprising the member according to claim 1.

14. A pressure support system, comprising:
a pressure generator for generating a flow of breathable gas; and
a patient interface for providing the flow of breathable gas to a self-ventilating patient, wherein the patient interface comprises the member according to claim 1.

* * * * *